United States Patent [19]

Johnson

[11] 4,157,498

[45] Jun. 5, 1979

[54] FLOW-THROUGH TYPE PARTICLE ANALYZING APPARATUS

[75] Inventor: Leighton C. Johnson, Edwardsburg, Mich.

[73] Assignee: Miles Laboratories, Inc., Elkhart, Ind.

[21] Appl. No.: 820,412

[22] Filed: Aug. 1, 1977

[51] Int. Cl.² ............................................. G01N 27/07
[52] U.S. Cl. .................................................. 324/71 CP
[58] Field of Search .................................... 324/71 CP

[56] References Cited

U.S. PATENT DOCUMENTS

| | | | |
|---|---|---|---|
| 3,165,692 | 1/1965 | Isreeli et al. | 324/71 CP |
| 3,638,677 | 2/1972 | Baccarini | 324/71 CP X |
| 3,714,565 | 1/1973 | Coulter et al. | 324/71 CP |
| 3,739,258 | 6/1973 | Karuhn et al. | 324/71 CP |
| 3,902,115 | 8/1975 | Hogg et al. | 324/71 CP |
| 3,924,180 | 12/1975 | Salzman et al. | 324/71 CP |
| 3,939,409 | 2/1976 | Hogg | 324/71 CP |
| 4,070,617 | 1/1978 | Kachel et al. | 324/71 CP |

Primary Examiner—Gerard R. Strecker
Attorney, Agent, or Firm—Roger N. Coe

[57] ABSTRACT

An improved flow-through type particle analyzing apparatus utilizing multiple electrodes to produce an electrical pulse upon sensing a particle passing through an aperture is provided with a well-shaped liquid sample receiving receptacle or reservoir which is positioned over said aperture and comprises an orifice electrode, made at least in part of a conductive material such as metal. The construction minimizes the sample volume required to properly wet and make electrical contact with the orifice electrode, and it also minimizes the flow path of aperture current thereby correspondingly minimizing electrical noise.

In a preferred embodiment means are incorporated for cleaning the particle analyzing apparatus in the immediate vicinity of the aperture, thereby minimizing the blockage and avoiding the necessity of dismantling the apparatus for cleaning.

5 Claims, 6 Drawing Figures

FLOW-THROUGH TYPE PARTICLE ANALYZING APPARATUS

FIELD OF THE INVENTION

The present invention relates to apparatus used in analyzing the dimensional characteristics of micron and submicron-sized bodies and more particularly, the invention relates to flow-through type apparatus in which sample volume required to properly wet and make electrical contact with the outer orifice electrode is minimized.

DESCRIPTION OF THE PRIOR ART

In recent years considerable attention has been given to automatic and semi-automatic instrumented microbiological and bacteriological assay systems. One approach which has achieved significant success is based on computer analysis of the output signal from sensing devices in flow-through systems. In systems having a sensor output coupled to the computing means, the specimen body or particle is suspended in a fluid medium and caused to flow through the sensing means in order to obtain the desired data. Such flow-through systems enable maximum advantage to be taken of the speed and utility of automatic and semi-automatic assay methods for handling test specimens.

Assay methods involving particle sensing means coupled to multi-channel analyzing means have been applied successfully, for example, to the study of bacteria, mammalian and fish blood, algae, inert dust, ocean sediments, fluid droplets and the like. Such methods include those set forth in U.S. Pat. Nos. 3,804,720 and 3,919,050, which are hereby incorporated by reference.

Examples of flow-through particle sensor apparatus include those using the well-known Coulter procedure described in U.S. Pat. Nos. 2,656,508 and 2,869,078, which are hereby incoporated by reference. In the Coulter procedure a particle suspended in an electrolyte is passed through an electrical field having dimensions related to those of the particle. This causes a momentary change in the electrical resistance in the ambit of the electrical field. This change of resistance diverts some of the excitation energy into associated electrical circuitry giving rise to an electrical signal. By counting the signals produced, a count can be obtained of the number of particles passing through the aperture.

In Coulter-type particle analyzing apparatus, the electrical field used for particle detection is formed in a passageway or aperture between two bodies of a liquid. The electrical excitation energy is coupled to these fluid bodies by means of electrodes immersed therein, the aperture being formed in an insulated wall between the fluid bodies. The electrical field is concentrated at the aperture which serves as the sensing zone and that field normally comprises an electrical current flowing through the aperture along with the physical flow of suspension. It will be appreciated that as a particle passes through the sensing zone it displaces its own volume of the electrolyte; this increases the resistance between the electrodes resulting in an electrical signal. The response depends substantially on the exposed cross-sectional area of the particle, residence time and its path through the aperture, and is usually independent of the dielectric properties of the particle.

In the typical particle sensor apparatus the electrically conductive fluid suspension is drawn through the electrical field as a result of pressure differential. One electrode is normally placed inside an electrically insulating vessel containing the aperture while the other electrode is conventionally mounted in a larger vessel containing the test specimen which is to be passed through the aperture.

It will be appreciated that the parameters of the sensor aperture must be carefully selected to obtain optimum performance for particle analysis. The aperture cannot be too large in diameter relative to the size of the particle since the resultant signal due to the passage of a particle may approach the electrical noise in the system. Conversely, the aperture should not be too small in diameter since this restricts fluid flow, requiring higher pressure differentials for a given flow rate and also may lead to plugging by debris suspended in the fluid.

For monitoring bacteria from body fluids, for example, it has been found that an aperture size of between about 10 microns and about 200 microns in diameter is suitable for use in the monitoring of particles having an apparent diameter larger than 0.1 micron. Normally, however, it is preferred to operate with an aperture size of from about 30 microns to about 100 microns for the routine monitoring of particles having an apparent diameter of 0.2 microns to 20 microns.

Conventionally, the output from the sensor is connected through suitable amplifying circuits to a pulse height analyzer which has means for correlating the height of the pulse with a corresponding storage increment called a channel number. Means are also normally provided for tabulating the number of pulses falling into a particular channel and for displaying the stored data as a hard copy readout. There also may be means provided for conversion to analog form for X-Y display on an oscilloscope or a X-Y hard copy plotter.

A suitable pulse height analyzer is the RIDL-34-20 manufactured by Radiation Instrument Development Laboratory, which is now a part of Searle Analytic, Inc., Des Plaines, Ill. 60018. This particular analyzer has 200 channels, but other analyzers having a greater or lesser number of channels can be employed. The RIDL-34-20 can be employed with a Hewlett-Packard 120B oscilloscope, marketed by Hewlett-Packard Company, San Diego, Calif. 92127, as a monitor and a Mosley 7035 X-Y plotter (also manufactured by Hewlett-Packard Company) can be used to provide analog readout.

One difficulty encountered in making analyses of the type referred to herein is with the amount of sample required for each analysis. Conventionally, flow-through systems require at least 12 milliliters of broth sample in order to wet the outer electrode. With increasing automation and the need for reproducing runs based on discreet aliquots of identical sample, there is a need for apparatus designed to minimize the amount of sample volume required for flow-through systems.

Another difficulty encountered with the design of flow-through systems has been the substantial electrical noise which occurs due to the flow of current through the electrolyte.

Aperture blockage has been another problem with flow-through systems. The use of variable apertures and other techniques have not overcome this problem. Accordingly, it has been necessary to periodically dismantle the apparatus of flow-through systems in order to clean the aperture.

In U.S. Pat. No. 3,714,565 the electrodes for a Coulter-type particle analyzing device are actually applied to the inner and outer surfaces of the insulating material containing the aperture. This apparatus does have an advantage of minimizing the flow of current through the electrolyte and thereby decreasing attendant electrical noise. However, the arrangement set forth in the patent does not minimize the sample volume required to properly wet and make electrical contact with the outer electrode. For operation, the described apparatus still requires that the outer electrode be placed in a beaker containing a substantial amount of sample. Moreover, the apparatus of the aforementioned patent does not incorporate any means for minimizing or clearing aperture blockage.

SUMMARY OF THE INVENTION

An object of the present invention is to provide improved apparatus for analyzing particles in flow-through systems.

Another object of the present invention is to provide apparatus which minimizes the sample volume required to properly wet and make electrical contact with the outer electrode of a particle sensing device which produces an electrical pulse upon sensing each particle.

Still another object of the present invention is to provide apparatus for minimizing electrical noise in flow-through type particle analyzing devices.

A further object of the present invention is to provide particle analyzing apparatus, utilizing a sensor to produce an electrical pulse upon sensing particles passing through an aperture, said apparatus having minimal aperture blockage problems.

Yet another object of the present invention is to provide means for cleaning the aperture used for sensing particles flowing through a particle sensing device.

In accordance with the present invention, an improved orifice electrode is disclosed for flow-through type particle analyzing apparatus which utilizes a sensor to produce electrical pulses upon sensing particles passing through an aperture. The orifice electrode, which is made at least in part of a conductive material such as metal, is formed into a well or cup-shaped reservoir for the liquid specimen or sample broth and positioned over the aperture of the particle sensing device. As little as 150 microliters of sample broth or specimen forms sufficient meniscus in the well or cup-shaped reservoir of the orifice electrode to properly wet the inner surface of the electrode and still provide sufficient sample for counting.

Incorporated in a preferred embodiment of the particle analyzing device are means for cleaning the area around the aperture in order to minimize blockage problems. Specifically, jets are incorporated which expose both sides of the aperture to the flow of fluid. Jet means are present inside the particle sensing device for circulating electrolyte in the vicinity of the aperture. Means are also present for projecting at least one jet stream into the outer electrode reservoir of the particle sensing device in order to clean the reservoir in the immediate vicinity of the aperture.

BRIEF DESCRIPTION OF THE DRAWINGS

Other and further objects, advantages and features of the invention will be apparent to those skilled in the art from the following detailed description thereof, taken in conjunction with the accompanying drawings, in which.

DESCRIPTION OF THE PREFERRED EMBODIMENTS

Flow-through type particle analyzing devices in accordance with the present invention comprise an orifice electrode forming a cup-shaped reservoir for containing suspended particles to be sensed and sized; receiving means for receiving suspended particles subsequent to the sensing and sizing thereof; an aperture interconnecting and in fluid communication with the orifice electrode and the receiving means; means for inducing liquid flow through said aperture thereby carrying suspended particles into the receiving means; an inner electrode inside the receiving means; and means associated with the orifice electrode and the inner electrode for electrically sensing and measuring characteristics of the particles passing through said aperture. In a preferred embodiment means are also present inside the receiving means for displacing electrolyte and suspended particles from the vicinity of the aperture. In another preferred embodiment means are present for rinsing or cleaning the orifice electrode reservoir.

Figure 3:
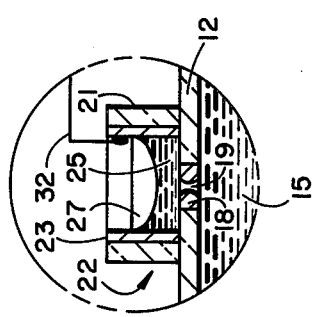
FIG. 3 is an enlarged diagrammatic side view of the orifice electrode portion of FIG. 1 indicated by phantom outline.
Figure 2:
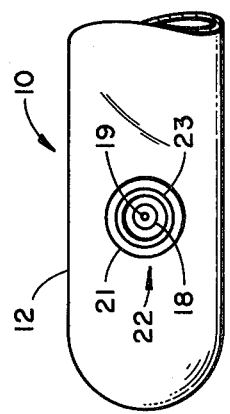
FIG. 2 is a partial top view of the flow-through type particle sensing device illustrated in FIG. 1 showing further details of the orifice electrode.
Figure 1:
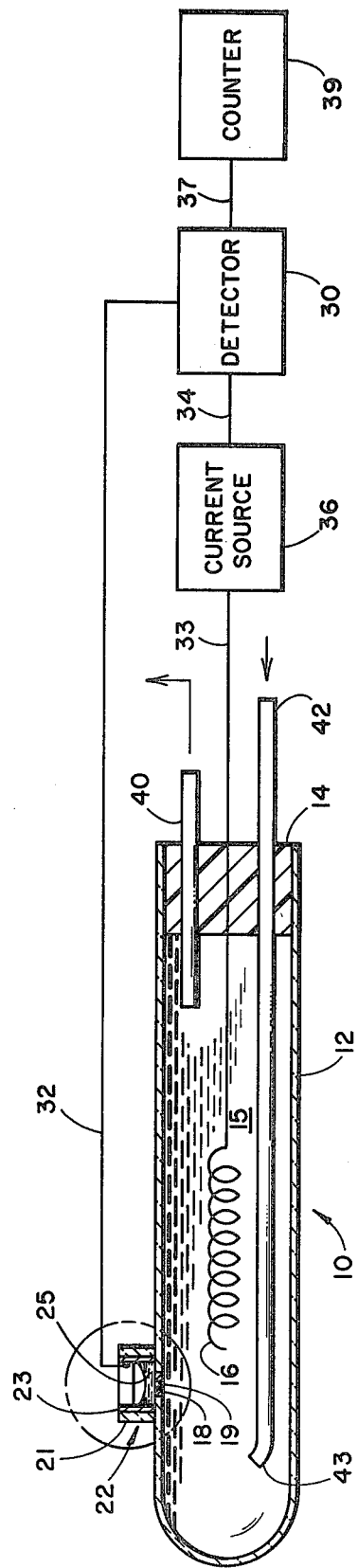
FIG. 1 is a diagrammatic side view, partially in cross-section, of a flow-through type particle analyzing device having sensing means and analyzing means which can be utilized in accordance with the present invention.

Referring now specifically to the drawings, a flow-through type particle sensing device 10 in accordance with the present invention is illustrated by FIGS. 1–3. Particle sensing device 10 is shown comprising tube shaped receiving means 12 having a single open end closed by stopper means 14. Receiving means 12 contains electrolyte 15 and an inner electrode 16 suspended in electrolyte 15. Insert 18, having an aperture 19, is sealingly mounted in a suitable accomodating opening in a side wall portion of receiving means 12. A cylindrical sleeve member 21 is sealingly attached at one end to the outer surface of receiving means 12 and forms therewith a cup-shaped receptacle or containing member 22. Sleeve 21 is positioned concentrically around insert 18 and aperture 19. An orifice electrode 23 in the form of a thin cylindrical sleeve is positioned telescopically within sleeve member 21. The containing member 22 forms a reservoir for a suspension, such as suspension 25, of particles which are to be analyzed by particle sensing device 10.

In FIGS. 1–3 orifice electrode 23 is illustrated as a cylindrical metal surface lining the inner surface of sleeve member 21, the latter serving as a support for the orifice electrode, thereby minimizing the amount of metal required for orifice electrode 23. The configuration of sleeve member 21 and orifice electrode 23 is such that a sample volume of only about 150 to about 300 microliters of particle suspension 25 is required to properly wet and make electrical contact with the orifice electrode. Actually, liquid suspension within the receptacle 22 forms a meniscus 27, as shown, providing good electrical contact with the orifice electrode.

Orifice electrode 23 is operatively connected to detector 30 by electrical connection 32. Detector 30 is also operatively connected to inner electrode 16 by means of current source 36, connection 34 and electrical connection 33, which passes sealingly through stopper 14. As set forth hereinafter, detector 30 electrically senses, measures and amplifies signals produced by changes in resistance in aperture 19 when particles pass through the aperture. Current source 36, which may be a battery, supplies the necessary current to operate detector 30. Detector 30 is further operatively connected to counter 39 by means of electrical connection 37, which counter counts the number of signals detected by detector 30. Detector 30, current source 36 and counter 39 are all well known electrical circuit components for use in sensing particles and are described, for example, in U.S. Pat. Nos. 2,656,508 and 2,869,078, which patents are hereby incorporated by reference. If desired, a cathode ray oscilloscope (not shown) can be utilized to visually display the shape of the current or voltage pulses which are detected.

A tube 40 also sealingly extends through stopper 14 into receiving means 12 as shown. By connecting tube 40 to a vacuum source (not shown) it is possible to draw particle suspension 25 through aperture 19 into receiving means 12 and count the particles as they pass through the aperture.

Figure 4:
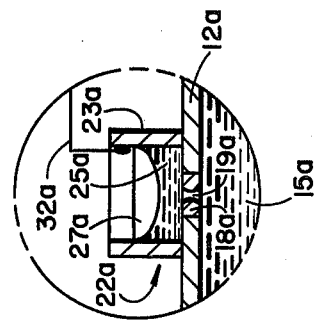
FIG. 4 is an enlarged diagrammatic side view of an alternative orifice electrode which can be used in place of that illustrated in FIGS. 1 to 3.

An alternate embodiment for orifice electrode 23 is illustrated in FIG. 4 in which parts corresponding to those of FIGS. 1-3 are indicated by the same numerals bearing the suffix a. For example, a portion of tube shaped receiving means 12a is illustrated having insert 18a and aperture 19a present in the side wall of said receiving means to provide a passageway through which suspension 25a can flow into receiving means 12a. Orifice electrode 23a provides a cup-shaped containing means for the particle suspension 25a. Orifice electrode 23a is sealingly attached to the receiving means 12a at its inner end and, unlike orifice electrode 23 of FIGS. 1-3, is totally self supporting. Thus, sleeve member 21 of FIGS. 1-3 is not required for this alternative embodiment, orifice electrode 23a forming, with receiving member 12a, a cup-shaped containing member 22a. Suspension 25a forms a meniscus 27a inside orifice electrode 23a as shown assuring good electrical contact between said electrode and suspension. Electrical connection 32a connects orifice electrode 23a with a detector (not shown in FIG. 4), such as detector 30 of FIG. 1.

In a preferred embodiment at least one fluid jet is used to remove material from the region around the aperture. Such jets facilitate cleaning between sampling and provide the necessary means for preventing and clearing aperture blockage. The jets are normally not used during the counting period. In order to remove debris and suspended material, particles, and the like away from the interior of aperture 19, for example, a tube 42 (FIG. 1) is provided which sealingly extends through stopper 14 into the interior of receiving means 12 as shown. By injecting fluid, such as saline solution, through tube 42 and out curved end 43 thereof located near aperture 19 debris, suspended material and the like which has collected inside receiving means 12 in the vicinity of aperture 19 can be pushed away and effectively removed from that vicinity. Thus, by injecting fresh electrolyte into tube 42 it is possible to prevent the accumulation of material in the vicinity of the inner surface of aperture 19 which could tend to block or otherwise clog it. Curved end 43 can be suitably positioned for maximum effectiveness and desired turbulence.

Figure 5:
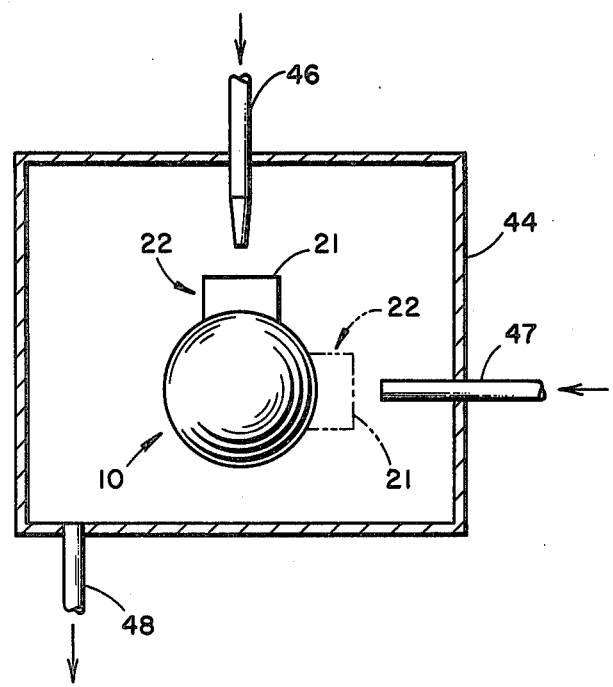
FIG. 5 is a diagrammatic end view, partially in cross-section, of the flow-through type particle sensing device of FIG. 1 shown inside a rinsing chamber.

A preferred embodiment for cleaning orifice 19 inside containing member 22 is illustrated in FIG. 5. In FIG. 5 flow-through type particle sensing device 10 of FIG. 1 is shown inside rectangular housing 44 with receptacle or containing member 22 in an upright position to receive sample from pipette 46 which extends through a wall portion of housing 44 and is located directly over said receptacle. After making a particle count, orifice 19 can be cleaned by axially rotating device 10 in a clockwise direction as viewed in FIG. 5 to the position thereof shown in phantom outline, wherein the open end of containing member directly opposite jet 47 which extends through a sidewall portion of housing 44. Saline solution and/or other suitable fluid injected through jet 47 into containing member 22 cleans orifice 19 therewithin. By continuing the rotation of particle sensing device 10 in a clockwise manner as viewed in FIG. 5 containing member 22 is once again positioned directly underneath pipette 46. Additional sample can then be placed into containing member 22 for analysis. Any liquid remaining inside containing member 22 escapes into housing 44 and is ultimately discharged through drain tube 48.

It will be understood that jet 47 can be repositioned and that other movement, such as lateral or axial movement, of device 10 relative to housing 44 can be made in order to effectively clean the inside of containing member 22. In addition, multiple jets 47 can be present.

Figure 6:
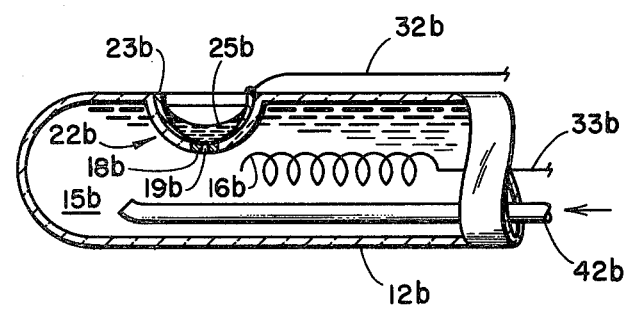
FIG. 6 is a diagrammatic side view, partially in cross-section, of another embodiment of a flow-through type particle sensing device which can be utilized in accordance with the present invention.

An alternative embodiment of a flow-through type particle sensing device in accordance with the present invention is illustrated in FIG. 6. For purposes of clarity parts in FIG. 6 corresponding to those of FIGS. 1 to 3 are indicated by the same numerals bearing the suffix b. In this embodiment there is no receptacle or orifice electrode which protrudes or extends from the surface of a tube-shaped receiving means. Instead, tube-shaped receiving means 12b itself is formed with a generally hemispherical cavity or depression comprising containing member 22b which serves as a containing means or receptacle for suspension 25b to be analyzed. Containing member 22b is formed with a suitable opening for sealingly accomodating an annular insert 18b formed with an aperture 19b. Containing member 22b accomodates therewithin orifice electrode 23b of complementary shape as shown. Electrical connection 32b is shown connected to orifice electrode 23b. The other electrode 16b is shown inside tube-shaped receiving means 12b and connected to electrical connection 33b. Tube 42b is positioned inside receiving means 12b in a manner similar to tube 42 in FIG. 1.

The tube-shaped receiving means (12, 12a and 12b) is preferably constructed of an insulating material, such as glass or plastic. The size of said receiving means is not critical and can be of any convenient size. The stopper means closing the end of the receiving means can be made of rubber, plastic, cork or any other suitable material.

Platinum is a preferred material for construction of both the outer orifice electrode and the inner electrode, since it possesses good electrical conductivity, it is inert and it is strong mechanically, especially if alloyed with a small percentage of iridium. Platinum can be fired onto glass and thus made to adhere to the glass. Platinum can also be suitably bonded to glass. In addition, platinum does not corrode easily. Other metals, such as silver, gold, stainless steel, German silver and tantalum, can also be used as electrode materials. Silver, while an excellent electrical conductor is soft mechanically and oxidises easily. It is more sensitive to corrosion than either platinum or gold. Gold, although soft, is a satisfactory electrode material, but is normally not used since it is nearly as expensive as platinum. Surgical-grade stainless steel is strong mechanically and does not corrode easily in most applications. It does have the advantage of cheapness relative to the cost of noble metals. It will be understood that the inner and outer electrodes of the present invention do not necessarily have to be constructed of the same materials.

While the inner electrode is shown in the form of a coiled helical configuration, it will be understood that the inner electrode could be any suitable form, such as a disc. The outer electrode can also take a variety of shapes. For example, it can take the tubular cylindrical shape shown in FIGS. 1-4, the generally hemispherical shape shown in FIG. 6, an elliptical configuration or other suitable shape. If desired, the outer electrode can also be formed simply as a metal strip or band inside the receptacle or containing member, such as containing member 22 of FIG. 1.

It has been found that saline solution can be used as electrolyte and also as the liquid used to form a suspension of particles in the outer electrode. Polyfuser saline prepared by the Boots Co. Ltd. of Nottingham, England is especially satisfactory because of its low particle background count and batch reproducibility.

Any suitable insulating material such as sapphire, corundum or other inert element can be used for insert means 18 forming aperture 19. This insert means is either fused into the side wall of the receiving means or otherwise suitably connected to the wall of the receiving means such that the aperture in the insert means provides an interconnecting passageway for suspended particles from sample receptacle into the receiving means. It will be understood that the aperture itself can be selected with respect to size, length and shape to optimize the measurements which are made.

From the foregoing, it will be seen that this invention is adapted to attain all of the ends and objects hereinabove set forth, together with other advantages which are obvious and inherent. An improved particle analyzing apparatus is disclosed which minimizes sample volume required to properly wet and make electrical contact with the outer electrode. The apparatus of the present invention also substantially eliminates or minimizes effects of debris, air bubbles and the like in the vicinity of the aperture, thereby permitting a high order of reliability to be achieved using the apparatus.

Although the present invention is particularly useful in sensing microorganisms such as bacteria, fungi, algae and yeast, the invention can advantageously be adapted for use with particles such as abrasives, foodstuffs, dyes, ceramics, pigments, polymer lattices, cement, powdered metals, and the like.

Obviously, many modifications and variations of the invention as hereinbefore set forth can be made without departing from the spirit and scope thereof and therefore only such limitations should be imposed as are indicated by the appended claims.

What is claimed is:

1. Flow-through type particle analyzing apparatus comprising in combination:
    means for containing an electrolyte, said means including a wall portion provided with an orifice,
    first electrode means formed into a configuration for holding between about 150 and about 300 milliliters of sample liquid suspension, said first electrode means being integral with said electrolyte containing means and positioned in registration with said orifice, said electrode arrangement minimizing the sample volume required and minimizing the flow path of aperture current to decrease electrical noise,
    a second electrode positioned within said electrolyte containing means and in electrical contact with the electrolyte therein, and
    means for inducing flow of sample suspension from said first electrode means through said orifice into said electrolyte containing means.

2. The apparatus of claim 1 in which each electrode is independently made from platinum, silver, gold, stainless steel, German silver or tantalum.

3. The apparatus of claim 1 which also contains means inside the electrolyte containing means for directing a flow of liquid to remove debris from the vicinity of the orifice.

4. The apparatus of claim 1 which also contains means for directing fluid against the outer surface of the first electrode.

5. A flow-through type electrode apparatus having an electrode structure for receipt of sample, said electrode structure formed into a configuration for holding between about 150 and about 300 milliliters of sample liquid suspension and positioned within a housing, said electrode structure being disposed within said housing in registration with an orifice through which said sample suspension flows and movable to first and second positions;
    means within said housing for dispensing sample;
    means within said housing for discharging a fluid under pressure;
    said dispensing means being positioned to dispense sample into said electrode structure in its said first position; and
    said discharging means being positioned to discharge fluid under pressure into said electrode structure when said electrode structure is in its said second position.

* * * * *